United States Patent [19]

Mueller et al.

[11] Patent Number: 4,861,358

[45] Date of Patent: Aug. 29, 1989

[54] BRANCH COUPLING FOR USE BETWEEN CAPILLARY COLUMNS OF GAS CHROMATOGRAPHS

[75] Inventors: Friedhelm Mueller, Linkenheim-Hochstetten; Horst Straub, Karlsruhe, both of Fed. Rep. of Germany

[73] Assignee: Siemens Aktiengesellschaft, Berlin and Munich, Fed. Rep. of Germany

[21] Appl. No.: 160,882

[22] Filed: Feb. 26, 1988

[30] Foreign Application Priority Data

Mar. 9, 1987 [DE] Fed. Rep. of Germany ....... 3707488

[51] Int. Cl.$^4$ ............................................. B01D 15/08
[52] U.S. Cl. .......................................... 55/386; 55/67; 285/911; 285/917
[58] Field of Search ................ 55/67, 197, 386; 285/334.2, 370, 397, 911, 917

[56] References Cited

U.S. PATENT DOCUMENTS

| 4,083,702 | 4/1978 | Hartigan et al. | 55/386 X |
| 4,313,828 | 2/1982 | Brownlee | 55/386 X |
| 4,394,263 | 7/1983 | Dosch et al. | 55/386 X |
| 4,407,482 | 10/1983 | Daghe et al. | 285/917 X |
| 4,451,363 | 5/1984 | Brownlee et al. | 55/386 X |
| 4,451,364 | 5/1984 | Higgins et al. | 55/386 X |
| 4,529,230 | 7/1985 | Fatula, Jr. | 285/911 X |
| 4,551,249 | 11/1985 | Shackelford et al. | 55/386 X |
| 4,586,732 | 5/1986 | Anderson, Jr. | 285/397 X |
| 4,669,756 | 6/1987 | Cassaday et al. | 55/386 X |
| 4,690,437 | 9/1987 | Anderson, Jr. | 55/386 X |

FOREIGN PATENT DOCUMENTS

| 0003617 | 8/1979 | European Pat. Off. | |
| 2840612 | 3/1980 | Fed. Rep. of Germany | 55/386 |
| 2491215 | 4/1982 | France | |
| 1562664 | 3/1980 | United Kingdom | |
| 2097694 | 11/1982 | United Kingdom | |

Primary Examiner—Robert Spitzer
Attorney, Agent, or Firm—Mark H. Jay

[57] ABSTRACT

A connecting capillary tube is arranged in a branch coupling and is shorter than the guide bores into which separation columns are introduced. The ends of the separation columns slide automatically over the ends of the connecting tube. The connecting tube is sealed with metal disks instead of graphite ones. The flush gas conduits are so arranged that the dead spaces can be well flooded, reducing adsorption of sample and increasing the performance of the gas chromatograph.

10 Claims, 1 Drawing Sheet

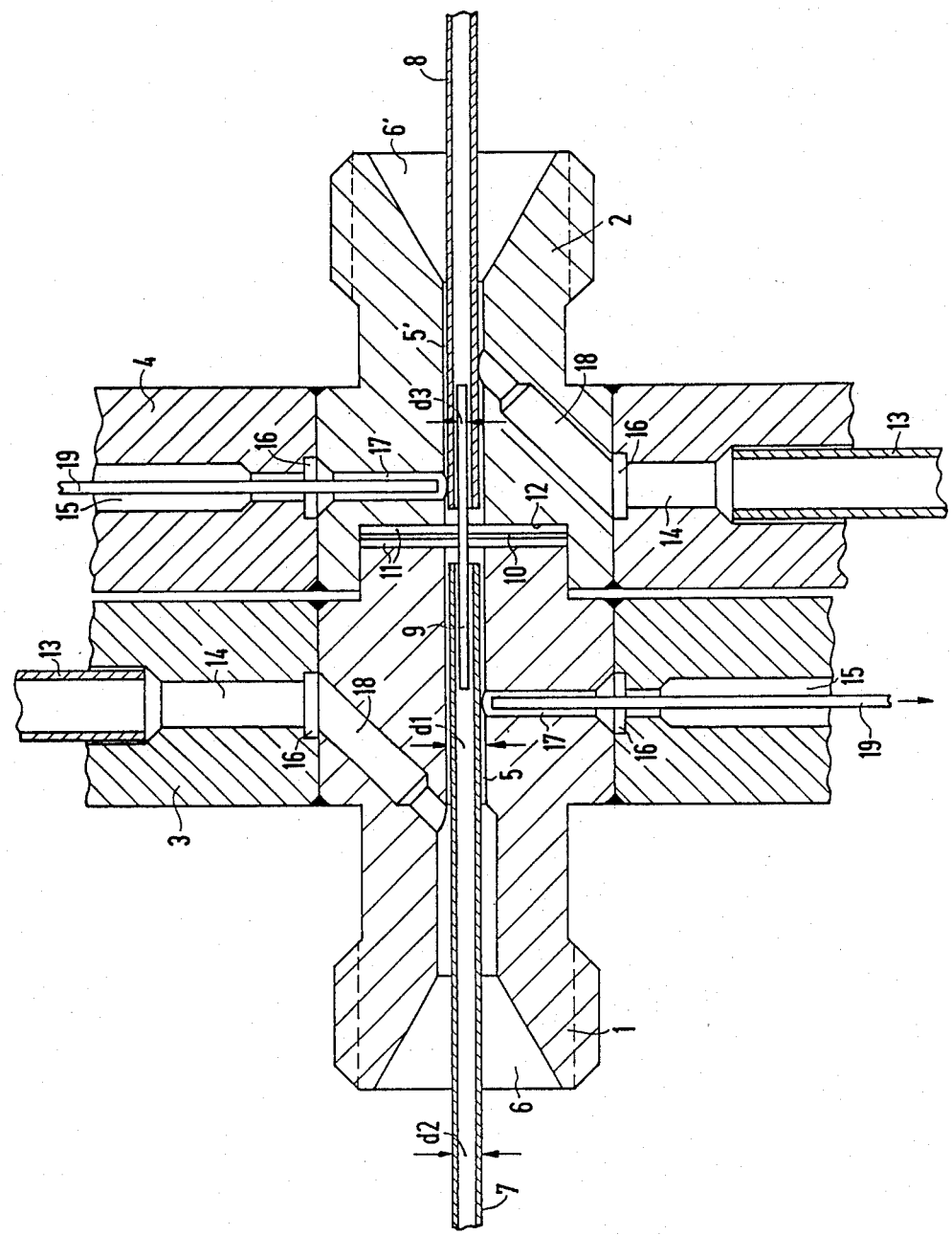

BRANCH COUPLING FOR USE BETWEEN CAPILLARY COLUMNS OF GAS CHROMATOGRAPHS

BACKGROUND OF THE INVENTION

The invention relates to a branch coupling of the type which is used to change the flow of gas between two gas chromatograph capillary columns.

A branch coupling of this type is shown in FIG. 3 of German Pat. No. 26 55 387. In this device, the capillary columns are connected together by a connecting capillary tube. This tube extends from the housing at both sides, and the separation columns are normally slipped onto the ends of the tube. This requires skill and dexterity to avoid damaging the columns and/or the tube. Furthermore, because the connecting tube is relatively long, it has a high flow resistance. As a result, the sample dwells for a relatively long time in the connecting tube, impairing separation in the columns.

This known device also has a cylindrical graphite seal which seals the connecting tube to the center of the housing. The graphite is compressed when the housing parts are screwed together.

Because graphite is used, the seal must be relatively large because it will not withstand high compression. Furthermore, graphite is disadvantageous because it absorbs parts of the gas sample and air and oxygen may diffuse through it.

It would be advantageous to provide a branch coupling which would decrease the flow resistance in the connecting capillary tube, which would reduce or prevent adsorption on seals and in nonflooded dead space, and which would be easier to assemble.

SUMMARY OF THE INVENTION

In accordance with the invention, a branch coupling has first and second mating housing sections. Each of the sections has an axially extending guide bore. The guide bores have like dimensions and are coaxial when the housing sections are mated together. A disk which is made of a high density and low adsorbency material is located between the housing sections in such a manner as to be axially aligned with the guide bores. The disk supports a connecting capillary tube which is centrally mounted to it and extends part way into each of the guide bores. The outer diameter of the connecting capillary tube exceeds the difference between the inner diameter of the guide bores and the outer diameter of the capillary columns which are to be used with the branch coupling. Each of the housing sections has a means for feeding and draining gas into and from a corresponding one of the guide bores.

By so dimensioning the connecting capillary tubes and the guide bores, the capillary columns are guided by the guide bores and little or no force is applied to the connecting capillary tube. This minimizes the likelihood of breaking it. Further, flow resistance is reduced because the connecting capillary tube is shortened. As a result, the sample dwells for a shorter time in the connecting capillary tube.

The packing seal is advantageously metal, and greater compressive forces can be exerted on it. This permits better sealing to be achieved using a smaller seal. Since metal adsorbs little if anything, adsorption is decreased. The design permits unflooded dead spaces to be reduced.

BRIEF DESCRIPTION OF THE DRAWING

Exemplary and non-limiting preferred embodiments of the invention are shown in the drawing, which is a cross-sectional view of a preferred embodiment of the invention.

DETAILED DESCRIPTION OF PREFERRED EMBODIMENTS

Housing sections 1 and 2 are generally cylindrical. Each of the sections 1 and 2 has a welded-on annular flange (3 and 4 respectively). The flanges 3 and 4, and therefore the housing sections 1 and 2, can be tightly braced against each other, as by clamps (not shown).

Sections 1 and 2 have like-dimensioned coaxial guide bores 5 and 5' respectively. Sections 1 and 2 also have funnel-shaped ends 6 and 6' respectively, at which the guide bores 5 and 5' terminate. The ends 6 and 6' are shaped to receive the seals (not shown) for capillary separation columns 7 and 8. These columns 7 and 8 are not part of the invention, but as is described below, the invention is designed to accommodate them.

A connection between the columns 7 and 8 is established through a connecting capillary tube 9. The connecting tube 9 is supported and dimensioned so that it extends approximately half-way into each the guide bores 5 and 5'. Furthermore, the outside diameter d3 of the connecting tube 9 is chosen to be larger than the difference between the diameter d1 of the guide bores 5 and 5' and the outer diameter d2 of the columns 7 and 8. This construction makes it easy to slide the columns 7 and 8 over the ends of the connecting tube 9 since the ends of the columns 7 and 8 are guided by the guide bores 5 and 5' and little or no force is applied to the connecting tube 9.

The connecting tube 9 is coaxially fastened to the center of a disk 10. The disk 10 is of a highly dense and minimally adsorbent material; preferably, the disk 10 is metal and is advantageously silver. Similarly dimensioned sealer disks 11 can be slipped onto the connecting tube 9 on both sides of the metal disk 10, but this is not required. The disk 10 (and disks 11 if used) are all contained in a flat cylindrical chamber which is formed between a cylindrical recess in the front face of section 2 and a mating cylindrical projection on the front face of section 1.

Parts 1 and 2 can be tightly abutted against each other, exerting considerable pressure on the disks 10 and 11. This permits the same sealing function to be carried out using smaller disks.

Gas is introduced into, and drained from, each of the bores 5 and 5'. Accordingly, each of the flanges 3 and 4 contains a socket 13 into which a gas feed pipe may be introduced and a drain bore 17 into which a capillary tube 19 may be introduced. The drain bore 17 is dimensioned such that the capillary tube 19 can be press-fit into it just to the depth of the guide bores 5 and 5' to act as a drain choke.

When gas is fed in, it passes through the socket 13, a radially extending bore 14, and thence in an annular channel 16. Between the channel 16 and each of the guide bores 5 and 5' is a feed bore 18 which is at an acute angle to the guide bores 5 and 5' and is between their ends 6 and 6'. This construction permits all interior volumes to be flooded with gas, preventing dead spaces from arising.

Gas is drained out of the system via two routes. When the gas exits the guide bores 5 and 5', it passes through the capillary tubes 19. Where the gas circumvents the drain bores 5 and 5', it passes through the channels 16 into outlet bores 15, and thence to be outside.

Those skilled in the art will understand that changes can be made in the preferred embodiments here described, and that these embodiments can be used for other purposes. Such changes and uses are within the scope of the invention, which is limited only by the claims which follow.

What is claimed is:

1. A branch coupling for use between capillary columns of gas chromatographs, comprising:
   first and second mating housing sections each having an axially extending guide bore, the guide bore being different from and not including the capillary columns, and being coaxial when the housing sections are mated together;
   a high density and low absorbency disk which is axially aligned with the guide bores and is located between them between the housing sections;
   a connecting capillary tube which is centrally mounted to the disk, which extends only part way into each of the guide bores, and which satisfies the relationship $$d3 > d1 - d2$$

when d3 is an outer diameter of the connecting capillary tube, d1 is an inner diameter of each of the guide bores, and d2 is an outer diameter of each capillary column which is to be used with the branch coupling; and
   first and second means for feeding and draining gas into and from a corresponding one of the guide bores.

2. The coupling of claim 1, wherein each of the housing sections is cylindrical and has a flange, the flanges abutting each other when the sections are mated together.

3. The coupling of claim 2, wherein each of said first and second means is mounted to a corresponding one of the flanges wherein each means is so configured that gas feeds and drains extend radially in each flange.

4. The coupling of claim 2, wherein each flange contains an annular groove which is coaxial with a corresponding one of the guide bores, each of said grooves communicating with a gas feed bore and a gas drain bore.

5. The coupling of claim 4, wherein a gas feed bore is located in each of the housing sections and extends between the guide bore and the annular groove at an acute angle with respect to the guide bore.

6. The coupling of claim 1, wherein the disk is received within a chamber formed by a recess in one of the housing sections and a mating projection in the other one of the housing sections.

7. The coupling of claim 1, wherein the connecting capillary tube extends approximately half way into each of the guide bores.

8. The coupling of claim 1, wherein a drain bore is located in each housing section to drain gas from a corresponding one of the guide bores and said drain bore is dimensioned to tightly receive a capillary tube, whereby the capillary tube functions as a drain choke.

9. The coupling of claim 1, wherein the disk is of metal.

10. The coupling of claim 1, wherein there are three disks, with one disk being mounted to the tube, the other two disks being placed on both sides of said one disk and being slipped onto said connecting capillary tube.

* * * * *